United States Patent [19]

Fields

[11] 4,058,113
[45] Nov. 15, 1977

[54] TIME PERCEPTION DEVICE

[76] Inventor: Louis G. Fields, 11662 Sunset Blvd., Los Angeles, Calif. 90049

[21] Appl. No.: 631,472

[22] Filed: Nov. 13, 1975

[51] Int. Cl.$^2$ ............................................. A61B 5/16
[52] U.S. Cl. ................................. 128/2 N; 35/22 R; 273/1 E
[58] Field of Search ....................... 128/2 N; 273/1 E; 35/22 R

[56] References Cited

U.S. PATENT DOCUMENTS

| | | | |
|---|---|---|---|
| 1,564,138 | 12/1925 | Rowland | 35/22 R X |
| 2,341,678 | 2/1944 | Wickes | 35/22 R X |
| 2,678,692 | 5/1954 | Ranseen | 128/2 N |
| 2,984,017 | 5/1961 | Pask | 35/22 R X |
| 3,869,812 | 3/1975 | Arakelian et al. | 35/22 R |
| 3,892,053 | 7/1975 | Booher | 35/22 R |

OTHER PUBLICATIONS

Fields, L. G., *Dig. of 7th Intern. Conf. on Med. & Biol. Enging.*, p. 494, 1967.

Weber, D. S., *Perceptual and Motor Skills*, 21: pp. 863–866, 1965.

*Primary Examiner*—Kyle L. Howell
*Attorney, Agent, or Firm*—Charles H. Schwartz

[57] ABSTRACT

A time perception test instrument for performing a self-administered time perception test by a test subject, including a plurality of individual flashing lights arranged in an array and with all of the lights except one flashing intermittently at regular intervals and with one of the lights flashing at irregular intervals and with a plurality of test buttons corresponding in number to the flashing lights and with one test button associated with each flashing light to allow the test subject to select any individual one of the flashing lights judged by the test subject to be the light flashing at irregular intervals and with a random sclector for randomly selecting one of the plurality of lights to flash at irregular intervals after each selection by the test subject. A coincidence detector produces a coincidence signal when the test subject selects a particular one of the flashing lights which is flashing at irregular intervals.

25 Claims, 3 Drawing Figures

TIME PERCEPTION DEVICE

BACKGROUND OF THE INVENTION

The present invention is directed to a time perception test instrument for performing a self-administered time perception test by a subject. This test may also be thought of as a test of cognition by the subject. It has been shown that individuals with impairment of cerebral function may show impairment in their ability to perceive or respond to time. Specifically, it has been shown that uremic toxicity may be determined using a time perception test which may be self-administered by the patient. The time perception test instrument of the present invention may be, therefore, used as an automated aid to scheduling artificial kidney treatment by measuring the mental performance decrement as well as providing an assesment of any other factors which may cause either permanent or temporary organic impairment of cerebral function.

Chronic intermittent hemodialysis is currently maintaining life in otherwise terminal uremics suffering from kidney disease. Unfortunately, the treatment intervals are usually determined empirically or scheduled to be convenient to the hospital personnel. The difficulties are that insufficient dialysis presents the risk of long term, low grade toxemia. On the other hand, with excessive dialysis, there is the added risk of the dialysis procedure itself, plus the additional cost. As mental toxicity is an early manifestation of the uremic state, the use of physchodynamic performance tests, such as the time perception test of the present invention, to objectively indicate the level of toxicity and the need for dialysis, is of great value in scheduling dialysis.

Assesment of the severity of uremia and the adequacy of the therapy for this condition is hampered today by the lack of sensitive, accurate and easily performed measurements of uremic toxicity. Although many chemical tests have been proposed, and have actually been used to asses clinical status in renal failure, these tests may not reflect physiological or behavioral changes in the uremic patients, which changes may be very subtle. Moreover, these tests must be performed by a trained technician and take time and cost money to perform. Also, the tests usually require a blood sample and the constant taking of blood could endanger the use of the vein for dialysis. It has been determined that several parameters of neurological function are altered in uremia and it has been recommended that a measurement of the degree of alteration may be used to assess the severity of uremic toxicity. However, the previous tests for quantitatively assessing the abnormality is often limited by insensitivity, poor reproducibility, the need for complex and expensive machinery, and the requirement for constant attendance by a well trained technician.

As indicated above, perception of short-time intervals is altered in a variety of conditions that effect the central nervous function even though some of these factors exhibit only subtle effects on other aspects of brain function. The present invention is, therefore, an apparatus to measure this cerebral function by a simple, easily repeatable, self-administered test. Specifically, the invention is directed to apparatus which measures a subject's ability to detect the presence or absence of equality in duration of a series of sequential periods between brief flashes of light. The apparatus of the present invention is an improvement on earlier devices which have been described in the literature and, specifically, the present invention includes a significant improvement over these earlier devices.

In the devices of the prior art, the test subject is presented with an array of flashing lights, all of which flash at irregular intervals except one. The test subject has to choose the one flashing light which is flashing at a regular rate. After the selection, a new light is randomly selected to be regular with the remaining lights flashing at an irregular rate. The present invention provides an improvement over the prior art devices since the test provided by the present invention is not too difficult and is a true test for the measuring of mental performance decrement. The test provided by the present invention is not tedious and fatiguing for the test subject and does not create extraneous barriers to the test being one of a true test of mental impairment. With the test provided by the present invention it is simple to orient the test subject and it is not necessary that technical personnel be available so that the test is truly self-administered. The present invention also includes an automatic time penalty, which records a completed trial and randomly chooses a new irregular light if the test subject does not make a selection within a predetermined period of time.

The present invention provides a test subject with a completely opposite task to that of the prior art devices, i.e., choosing from an array of lights wherein only one light is flashing at an irregular rate. This choosing of the one light flashing at an irregular rate has been found to be significant improvement over the prior art devices, since it is truly a test of mental impairment. Moreover, the present invention includes a number of other improvements so that the time perception test instrument of the present invention is a more useful instrument for the assessment of central nervous system function.

The test subject is presented with nine intermittently illuminated pushbuttons mounted in an array and with eight of the buttons flashing at closely regular intervals but asynchronously with a particular pattern such as 0.1 seconds on and 0.6 seconds off and up to $\pm$ 10 percent. The slight differences between the regular oscillator prevents the regularly flashing lights from flashing in a regular pattern so that the test subject could pick out the irregularly flashing light through a pattern recognition and some method should be used, such as the above, so that the oscillators are asynchronous relative to each other, so as to prevent pattern recognition. One of the illuminated pushbuttons, which is randomly changed after each selection by a test subject, flashes in an irregular sequential pattern, such as 0.1 seconds on and 0.4 seconds off, 0.1 seconds on, and 0.8 seconds off, etc. The degree of irregularity of the irregularly flashing buttons may be controlled by a manual control means. The test subject is requested to examine each lighted pushbutton in turn, and to press the particular button which appears to the test subject to be the irregularly flashing lighted button. After each selection by the test subject or after a predetermined period, such as 45 seconds, whichever occurs first, the test instrument omits an audible signal, records a completed trial, and, again, randomly selects one lighted pushbutton to flash irregularly. The number of trials and the number of correct selections may be read from a digital display and this digital display may be hidden from view of the test subject by a lockable means. When a predetermined number of trials, such as 10 trials, are completed, all of the lights are turned off.

The display generator consists of 9 regular oscillators corresponding in number to the pushbuttons, one irregular oscillator, and a random number generator. The random number generator consists of a rapidly cycled zero-to-eight counter that is briefly activated each time the instrument is turned on, one of the lighted buttons is pressed, or after the predetermined period, such as 45 seconds, have elapsed with no selection by the test subject. This random number generator determines which of the nine lights is to be driven by the irregular oscillator and, in particular, selects a particular gate to pass the output of the irregular oscillator rather than the output of a regular oscillator associated with the gate.

The random generator also determines which one of a plurality of coincidence detectors may provide an output signal, so that a count is entered in a correct score counter when the correct lighted button is pressed. A separate circuit records the total number of times a selection of a lighted button is made, including the number of times that the predetermined period of time, such as 45 seconds, has elapsed without a selection. All of the lights may be turned off at the end of a predetermined number of tests, such as ten trial selections. A test subject can learn to operate the instrument and self-administer the test after a short period of instruction. The control of irregularity of the irregular oscillator may be manipulated by the technician to aid in the learning cycle of the instrument. Specifically, the degree of irregularity may be controlled to be quite severe so that it is obvious to the test subject which of the lights is flashing in an irregular pattern and with the degree of irregularity controlled to be closer to the regularly flashing lights so as to make the test more severe. Also, the audio output may be coupled to the irregular oscillator and one of the regular oscillators through a switch, to provide an audio output corresponding to the flashing of the lights. This may help the test subject to understand the difference between the outputs of the oscillators.

It should be appreciated that although the test instrument is described with reference to a measurement of uremic toxicity, the instrument may also be useful for objective measurements in a variety of conditions, including brain tumors and the effects of toxic materials, such as drugs and alcohol.

A clearer understanding of the invention will be had with reference to the following description and drawings wherein.

Figure 1:
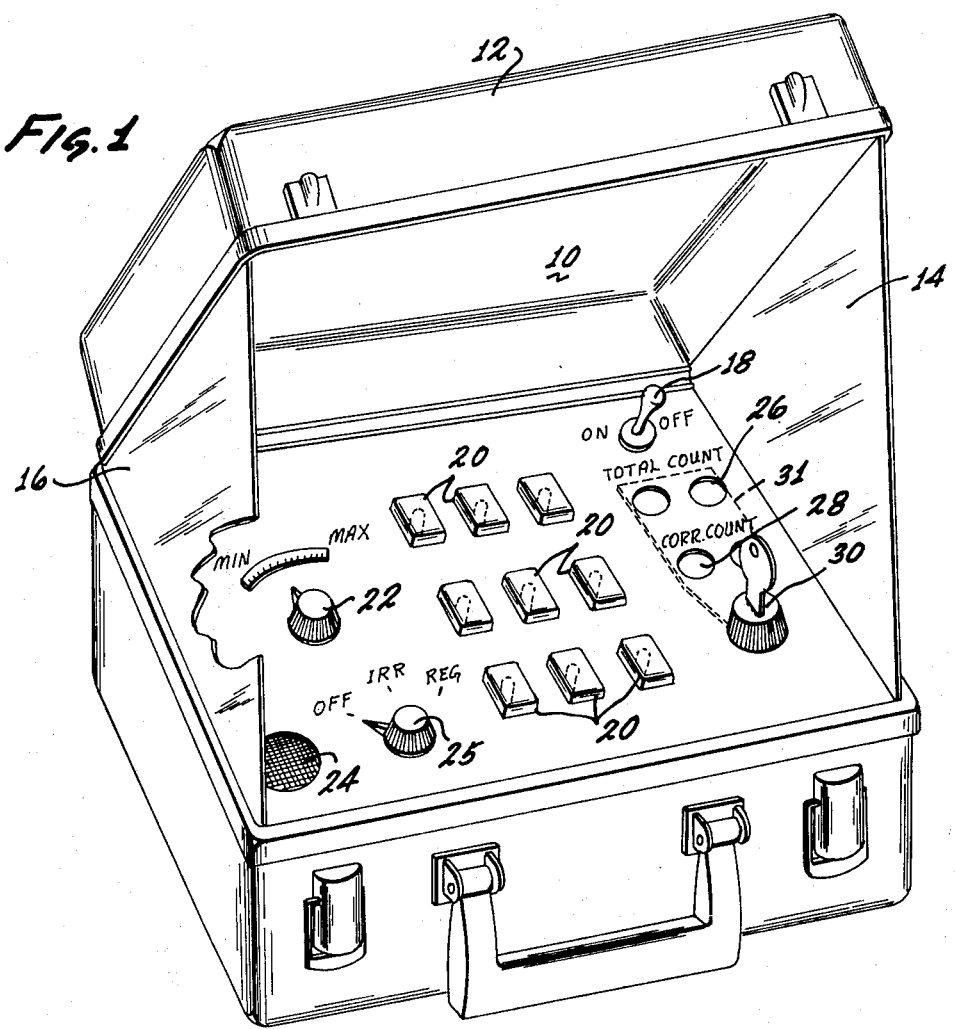
FIG. 1 illustrates the time perception test instrument of the present invention showing the front panel of the device and showing the instrument encased in a portable carrying case.

In FIG. 1 of the time perception test instrument 10 of the present invention is shown encased in a small luggage-type case 12 so as to be portable. A pair of shield members 14 and 16 may be included so as to permit the operation of the device in brightly lighted rooms.

The instrument 10 includes an on-off switch 18 to control the operation of the instrument. A plurality of lighted pushbuttons, 9 in number, are arranged in an array and these pushbutton individually flash and with one of the pushbuttons flashing in an irregular pattern and with the other 8 pushbuttons flashing in a regular pattern. A control knob 22 controls the degree of irregularity of the pushbuttons flashing at an irregular rate. A loud speaker 24 allows an audible tone to be heard by the test subject. A switch 25 controls the coupling of the irregular oscillator or one of the regular oscillators to the loud speaker 24 so that the test subject can have the benefit of an audio representation of the flashing pattern as a learning aid also as an auxiliary testing device.

The instrument 10 also includes a pair of counters 26 and 28 having visual displays corresponding to the total count and the correct count which occur during the test by the test subject. The display of the counters is concealed and the display may be revealed using a lock switch 30 to swing away a shield 31.

Figure 2A:
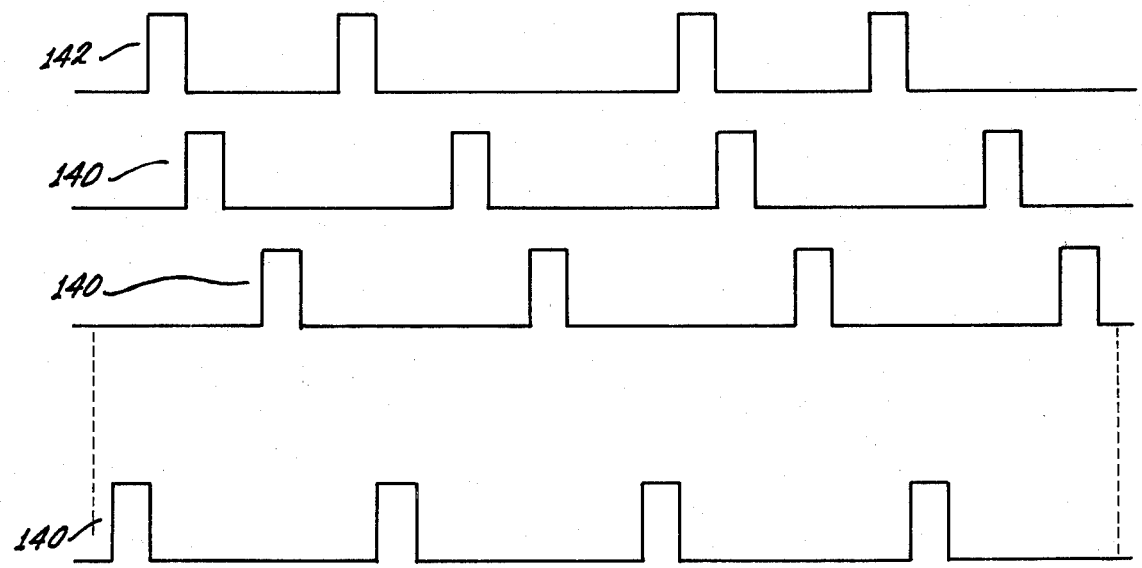
FIG. 2a illustrates waveforms showing the outputs of the irregular oscillator and the regular oscillators.
Figure 2:
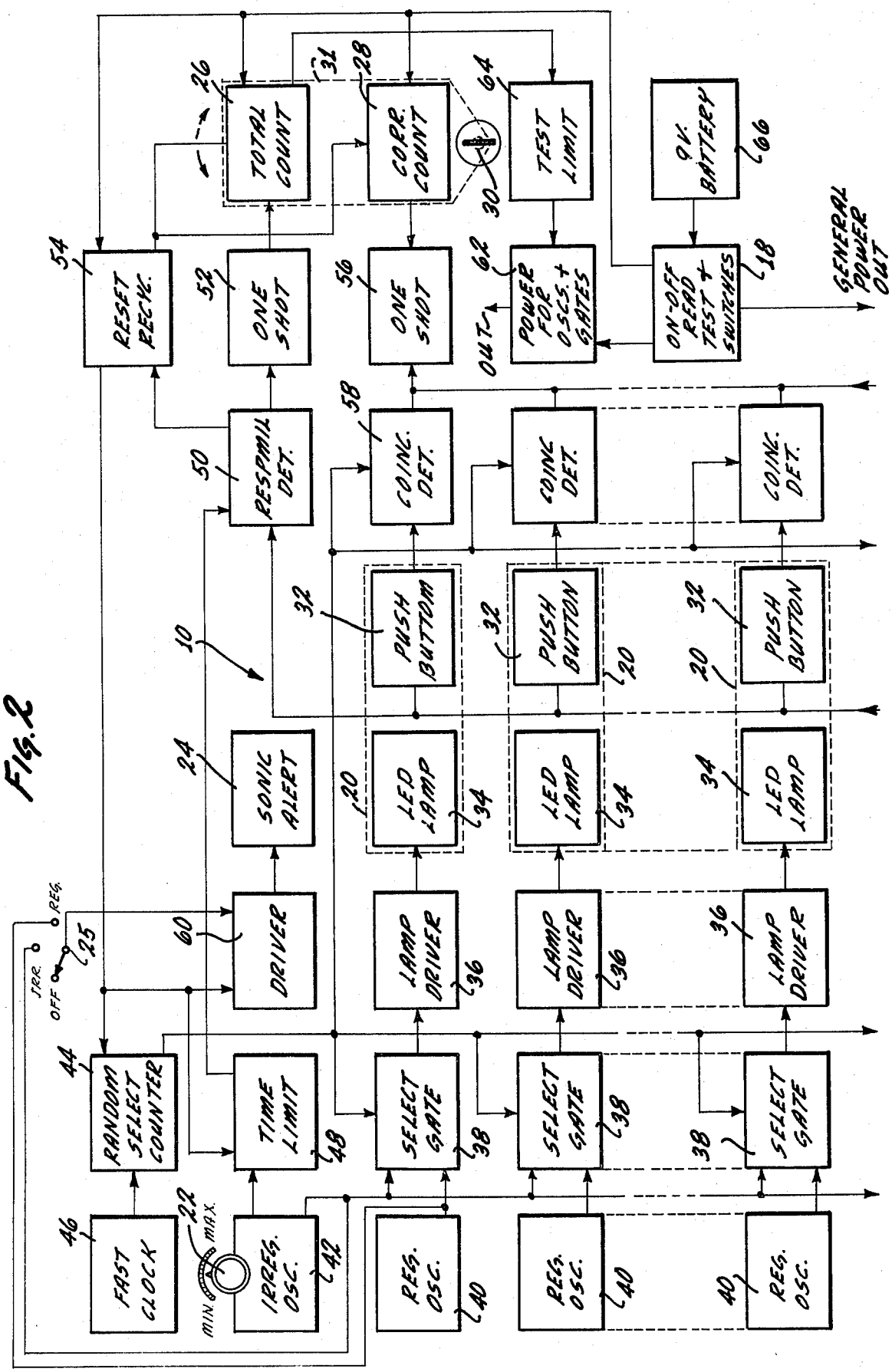
FIG. 2 illustrates a block diagram of the time perception test instrument of the present invention.

FIG. 2 illustrates a block diagram of the time perception test instrument of present invention 10. In FIG. 2 each of the lighted pushbuttons 20 is shown to be composed in a unit including a pushbutton switch 32 incorporating an LED lamp 34. Each LED lamp 34 is mounted within the pushbutton to make the lighted pushbuttons 20 shown in FIG. 1. Associated with each of the LED lamps 34 is a lamp driver 36 so there are a total of 9 lamp drivers 36 corresponding in number to the number of LED lamps 34.

Each of the lamp drivers 36 receives as its input signal an output from a selector gate 38. There are a total of 9 selector gates corresponding in number to the LED lamps 34. Associated with each of the selector gates is a regular oscillator 40 so that each selector gate 38 receives as one input an output from a regular oscillator 40. Each regular oscillator produces an asymmetrical oscillation pattern such as a pattern 0.1 seconds on, and approximately 0.6 seconds off and ± 10 percent as shown by waveforms 140 in FIG. 2a which differ in phase but have the same frequency pattern. It is to be appreciated, of course, that this pattern could be varied, but normally it is found that an asymmetrical pattern such as described above provides for an effective test of the test subject. In addition, the oscillators relative to each other are asynchronous, because of their slight differences, and this prevents pattern recognition.

Each of the select gates 38 also receive as an alternate input the output from an irregular oscillator 42. The irregular oscillator also provides an asymmetrical pattern such as an irregular sequential pattern of 0.1 seconds on, 0.4 seconds off, 0.1 seconds on, 0.8 seconds off as shown by waveform 142 in FIG. 2a. A manual control 22 may be used to vary the degree of irregularity of the output from the irregular oscillator. For example, the pattern described above, which has a ratio of irregularity of two to one could be a typical degree of irregularity and the manual control 22 may control the irregular oscillator to put out an oscillatory pattern having a lesser degree of irregularity such as 0.1 seconds on, 0.5 seconds off, 0.1 seconds on, 0.7 seconds off. This degree of irregularity may be controlled to be an even closer pattern to the pattern produced by the regular oscillators so as to increase the degree of difficulty of the time perception test or could be adjusted to decrease the degree of difficulty.

The degree of difficulty of the time perception test may be used as part of a learning mode, wherein a high degree of irregularity is initially chosen so that the test subject can familiarize himself with the testing procedure, and once the testing procedure is established in the test subject's mind, the degree of difficulty may be increased so as to make the selection of the irregularly flashing LED lamp 34 harder to perceive by the test subject. In addition, the switch 25, which would normally be in the off position, may also be used as part of a learning mode, wherein the irregular oscillator 42 and one of the regular oscillators 40 may be selectibly coupled to the speaker 24 to provide an audible output representative of the flashing lights. This audible output provides another way of showing the test subject the difference between the regular and irregular oscillations. In addition, this audible output can itself provide a test of mental impairment.

The particular one of the selector gates which is chosen to pass the output of the irregular oscillator 42, as opposed to the normally associated output from one of the regular oscillators 40, is determined by the random selector counter 44. A fast clock 46 drives the random selector counter 44 and the output from the random selector counter 44 determines which one of the 9 LED lamps 34 is to be driven by the irregular oscillator 42. The random select counter 44 is a rapidly cycled zero-to-eight counter that is briefly activated each time the instrument is turned on, one of the lighted buttons 32 is pressed, or after a predetermined period of time, such as 45 seconds, has elapsed with no selection by the test subject. This predetermined period of time is controlled by a time limit 48 which provides an output signal to a response detector 50.

The response detector 50 also receives an input signal each time one of the pushbuttons 32 is selected by the test subject. If the response detector receives an input signal, the response detector controls a one-shot multivibrator 52 to provide an input to the total counter 26 to step up one count. In addition, the output of the response detector 50 is coupled to a reset-recycle timer 54. The timer 54 provides a short pulse, such as ½ second to control the random selector counter 44 to randomly select a new one of the selector gates 38 to pass the output of the irregular oscillator 42 rather than one of the regular oscillators 40. In addition, the short pulse from the timer 56 acts as a reset pulse for the total count counter 26 and the correct count counter 38. Specifically, the counters 26 and 28 each include a flip/flop which are set by input signals from the one-shot 52 and a one-shot 56, and are reset by the short pulse from the timer 54. This insures that the counters 26 and 28 step up one count at a time.

The one-shot 56 receives as its input the output from any one of a plurality of coincidence detectors 58. The coincidence detectors 58 receive an input from the random select counter 44 and also an input from one of the pushbuttons 32. In this way, when the proper push-button 32 is selected by the test subject, which push-button corresponds to the count provided by the random select counter 44, which is also inputed to the appropriate one of the coincidence detectors 58, the particular coincidence detector produces an output signal to activate the one-shot 56. At that time, the output from the one-shot 56 sets the flip/flop within the counter 28 to move the counter ahead by one step and the output from the timer 54 provides a reset to the counter 28 so that it is ready to receive additional counts.

The output from the timer 54 is also applied to a driver 60 which activates the sonic alert or loudspeaker 24 to provide an audible tone to the test subject so the test subject knows that a new selection is to be made. If the test subject does not make a selection within a predetermined period of time, the time limit 48 through the response detector 50 and the timer 54 provides a signal to activate the driver 60 so that an audible alarm is sounded by the sonic alert 24. At the same time each time a selection is made or after a predetermined period of time the time limit 48 receives a signal from the timer 54 to reset the time limit.

The on-off switch 18 when initially turned on provides a signal to reset the counters 26 and 28 and in addition, provides a signal to start the timer 54 in its initial cycle. In addition, the output from the on-off switch 18 passes through a gate 62 to provide power for the oscillators and selector gates. At the end of a predetermined number of tests, which number is controlled by the test limit counter 64 which receives at its input the output from the total count counter 26, the test limit counter 64 controls the gate 62 to discontinue power to the oscillators and selector gates so that all of the LED lamps 34 are extinguished. The power for the instrument is provided by a battery such as a 9-volt battery 66.

In operation the 9 lighted pushbuttons flash at an average interval of approximately 0.7 seconds each. One lamp is irregular by a selectible amount (for example, 10 to 40%). The test subject judges a lamp to be irregular and pushes a button corresponding to that lamp and at that time a tone sounds and a concealed counter registers a total number of trials and a correct count. At random one of the 9 lamps is then selected to be the next irregular flashing lamp. If no selection is made in 45 seconds, a time penalty occurs which sounds a tone, registers an additional number in the total count, but no additional number in the correct count, and a new irregularly flashing lamp is again selected. After a preset number of trials, the lamps are extinguished and the results may then be read using a locked switch 30 which reveals the output of the counters 26 and 28. The lock switch may control a shield 31 which is positioned over the counters and is rotated away from the counters to reveal the total and correct count.

As shown in the block diagram of FIG. 2, in addition to the specific regular oscillators 40 select gates 38, lamp drivers 36, LED lamps 34, pushbuttons 32 and coincidence detectors 58, all of which are shown to be three in number. An additional six more of each of these is interconnected in the same manner shown in the block diagram, and as indicated in FIG. 2.

Although the invention has been described with reference to a particular embodiment, it is to be appreciated that various modifications and adaptations may be made, and the invention is to be only limited by the appended claims.

I claim:

1. Apparatus for performing a self-administered time perception test by a test subject, including:
   a plurality of individual light sources arranged in an array for providing a plurality of individual visual indications;
   first means coupled to the plurality of individual light sources for controlling the individual light sources to flash intermittantly and with all but one of the light sources controlled to flash at regular intervals and with one of the light sources controlled to flash at irregular intervals;
   a plurality of second means coupled to the plurality of individual light sources for selecting any individual one of the plurality of light sources judged by the test subject to be the light source flashing at irregular intervals;
   third means coupled to the first and second means for randomly selecting one of the plurality of light sources to flash at irregular intervals after one of the second means is selected by the test subject, coincidence means coupled to the first and second means to produce a coincidence signal when the test subject selects the particular one of the plurality of light sources flashing at irregular intervals;

a first counter means coupled to the coincidence means for counting each production of a coincidence signal to count the number of correct selections by the test subject; and a visual indicator coupled to the first counter means for visually displaying the number of correct selections and additionally including lockable means, including locked and unlocked positions coupled to the visual display for shielding the visual display when in the locked position and exposing the visual display when in the unlocked position.

2. The apparatus of claim 1 additionally including a second counter means coupled to the second means for counting the total number of selections by the test subject.

3. The apparatus of claim 2 additionally including visual indicators coupled to the first and second counter means for visually displaying the number of correct selections and the total number of selections and additionally including lockable means including locked and unlocked positions coupled to the visual indicators for shielding the visual displays when in the locked position and exposing the visual displays when in the unlocked position.

4. The apparatus of claim 1 additionally including timer means coupled to the third means for controlling the third means to randomly select one of the plurality of light sources to flash at irregular intervals after a predetermined period of time, if no second means is selected by the test subject during the predetermined period of time.

5. The apparatus of claim 1 additionally including fourth means coupled to the first and third means for turning off the flashing light sources after a predetermined number of selections by the test subject.

6. The apparatus of claim 1 wherein the first means controls the plurality of light sources to flash asymmetrically and with the one light source flashing in an irregular asymmetrical pattern.

7. The apparatus of claim 1 wherein the first means controls the plurality of light sources to flash asynchronously relative to each other.

8. The apparatus of claim 1 additionally including a fourth means coupled to the first means for providing a control for selecting the degree of irregularity of the flashing of the one light source.

9. The apparatus of claim 8 wherein the plurality of first means include means for controlling the plurality of light sources to flash asynchronously and for providing the one light source to flash in an irregular asynchronous pattern and with the fourth means providing a control for selecting the degree of irregularity of the irregular asynchronous pattern.

10. The apparatus of claim 1 additionally including audio means coupled to the third means for producing an audible output after each selection by the test subject.

11. The apparatus of claim 1 additionally including audio means coupled to the first means for producing separate audible outputs representative of the light sources flashing at regular intervals and the one light sourse flashing at irregular intervals.

12. Apparatus for performing a self-administered time perception test by a test subject, including;

a plurality of regular oscillators each producing oscillations at regular intervals;

a plurality of selector gates corresponding in number to the plurality of regular oscillators and with each selector gate having at least first and second oscillator inputs and at least one gate input and with each selector gate receiving an input at the first oscillator input from one of the regular oscillators;

at least one irregular oscillator producing oscillations at irregular intervals coupled to the second oscillator inputs of each of the plurality of selector gates;

a random selector producing a select signal coupled to the gates to control one of the gates to output the irregular oscillations and the remaining selector gates to output the regular oscillations;

a plurality of light sources corresponding in number to the selector gates and coupled to the outputs of the selector gates for flashing in accordance with the oscillations produced by the oscillators;

a plurality of test buttons corresponding in number to the number of light sources for selecting any individual one of the plurality of light sources judged by the test subject to be the light source flashing at irregular intervals, and a plurality of coincidence detectors corresponding in number to the number of test buttons and with each coincidence detector coupled to one of the test buttons and with all of the coincidence detectors coupled to the random selector and receiving the select signal to have one of the coincidence detectors produce a coincidence signal when there is a coincidence between the select signal and the actuation of the one of the test buttons corresponding to the light source flashing at irregular intervals.

13. The apparatus of claim 12 additionally including detector means coupled to the plurality of test buttons and to the random selector for activating the random selector to produce a select signal to randomly select one of the selector gates to control the one of the gates to output the irregular oscillations.

14. The apparatus of claim 13 additionally including a timer coupled to the detector means for controlling the detector means to actuate the random selector to provide the select signal to randomly select one of the selector gates to output the irregular oscillations after a predetermined period of time if no test button is activated by the test subject during the predetermined period of time.

15. The apparatus of claim 13 additionally including test limit means coupled to the light sources and the detector means for turning off the flashing light sources after a predetermined number of selections of the test buttons by the test subject.

16. The apparatus of claim 13 additionally including audio output means coupled to the detector means for producing an audible output after each selection of a test button by the test subject 17. The apparatus of claim 12 additionally including a first counter coupled to the plurality of coincidence detectors and responsive to any coincidence signals to count the number of correct selections by the test subject in accordance with the production of coincidence signals.

18. The apparatus of claim 17 additionally including a visual indicator coupled to the first counter for visually displaying the number of correct selections by the test subject and additionally including lockable means including locked and unlocked positions coupled to the visual display for shielding the visual display when in the locked position and exposing the visual display when in the unlocked position.

19. The apparatus of claim 17 additionally including a second counter coupled to the test buttons for counting the total number of selections by the test subject.

20. The apparatus of claim 19 additionally including visual indicators coupled to the first and second counters for visually displaying the number of correct selections and the total number of selections by the test subjects including lockable means including locked and unlocked positions coupled to the visual indicators for shielding the visual displays when in the locked position and exposing the visual displays when in the unlocked position.

21. The apparatus of claim 12 wherein the plurality of the oscillators control the plurality of light sources to flash asymmetrically and with the one light source flashing in an irregular asymmetrical pattern.

22. The apparatus of claim 12 wherein the plurality of oscillators control the plurality of light sources to flash asynchronously relative to each other.

23. The apparatus of claim 12 additionally including a manual control coupled to the irregular oscillator for providing a control for selecting the degree of irregularity of the flashing of the one light source.

24. The apparatus of claim 23 wherein the plurality of regular oscillators control the plurality of light sources to flash asynchronously and the irregular oscillator controls the one light source to flash in an irregular asynchronous pattern.

25. The apparatus of claim 12 additionally including audio output means coupled to at least one of the regular oscillators and the irregular oscillator for producing separate audible outputs representative of the oscillations at regular intervals and the oscillations at irregular intervals.

* * * * *